United States Patent
Kumar et al.

(10) Patent No.: US 9,943,702 B2
(45) Date of Patent: Apr. 17, 2018

(54) AUTOMATIC OPTIMAL IMRT/VMAT TREATMENT PLAN GENERATION

(71) Applicants: KONINKLIJKE PHILIPS N.V., Eindhoven (NL); The University of Texas M. D. Anderson Cancer Center, Houston, TX (US)

(72) Inventors: Prashant Kumar, Bangalore (IN); Karl Antonin Bzdusek, Madison, WI (US); Vaitheeswaran Ranganathan, Bangalore (IN); Matthew Palmer, Houston, TX (US); Michael Kantor, Houston, TX (US)

(73) Assignees: KONINKLIJKE PHILIPS N.V., Eindhoven (NL); BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 356 days.

(21) Appl. No.: 14/438,885

(22) PCT Filed: Oct. 18, 2013

(86) PCT No.: PCT/IB2013/059440
§ 371 (c)(1),
(2) Date: Apr. 28, 2015

(87) PCT Pub. No.: WO2014/068435
PCT Pub. Date: May 8, 2014

(65) Prior Publication Data
US 2015/0273238 A1    Oct. 1, 2015

Related U.S. Application Data

(60) Provisional application No. 61/719,528, filed on Oct. 29, 2012.

(51) Int. Cl.
| | | |
|---|---|---|
| A61N 5/00 | (2006.01) | |
| A61N 5/10 | (2006.01) | |
| G06F 19/00 | (2018.01) | |

(52) U.S. Cl.
CPC ......... A61N 5/1039 (2013.01); A61N 5/1031 (2013.01); A61N 5/1038 (2013.01);
(Continued)

(58) Field of Classification Search
CPC .... A61N 5/103; A61N 5/1031; A61N 5/1039; A61N 5/1045; A61N 5/1047
(Continued)

(56) References Cited

U.S. PATENT DOCUMENTS

| 7,369,645 | B2 | 5/2008 | Lane |
|---|---|---|---|
| 7,574,251 | B2 | 8/2009 | Lu |

(Continued)

FOREIGN PATENT DOCUMENTS

| JP | 2002210027 | 7/2002 |
|---|---|---|
| WO | 2011110958 | 9/2011 |

(Continued)

OTHER PUBLICATIONS

Bronnikov, A. V.; Reconstruction of Attenuation Map Using Discrete Consistency Conditions; 2000; IEEE Trans. on Medical Imaging; 19(5)451-462.

(Continued)

*Primary Examiner* — John Lacyk

(57) ABSTRACT

A therapy planning system (18) and method generate an optimal treatment plan. A plurality of objectives are automatically formulated (154) based on a plurality of clinical goals including dose profiles and priorities. The dose profiles and the priorities correspond to a plurality of structures including a plurality of target and/or critical structures identified within a planning image. Further, a plurality of
(Continued)

treatment plan parameters are optimized (156) based on the plurality of objectives to generate a treatment plan. The plurality of objectives are reformulated (162) and the plurality of treatment plan parameters are reoptimized (156) based on the reformulated plurality of objectives to generate a reoptimized treatment plan. The optimizing (156) is repeated based on the reformulated plurality of objectives to generate a reformulated treatment plan.

20 Claims, 2 Drawing Sheets

(52) U.S. Cl.
CPC ......... *A61N 5/1045* (2013.01); *A61N 5/1047* (2013.01); *G06F 19/3481* (2013.01); *A61N 5/1042* (2013.01)

(58) Field of Classification Search
USPC ........................................................ 600/1–8
See application file for complete search history.

(56) References Cited

U.S. PATENT DOCUMENTS

| 7,899,517 B2 | 3/2011 | Kindlein et al. |
| 2011/0053564 A1 | 3/2011 | Imaeda |
| 2011/0130614 A1 | 6/2011 | Schulz et al. |
| 2012/0136677 A1 | 5/2012 | Ziegenhein et al. |

FOREIGN PATENT DOCUMENTS

| WO | 2011154853 A1 | 12/2011 |
| WO | 2012024448 A2 | 2/2012 |
| WO | 2012045163 A1 | 4/2012 |

OTHER PUBLICATIONS

Castadot, P., et al.; Adaptive Radiotherapy of Head and Neck Cancer; 2010; Semin. Radiat. Oncol.; 20:84-93.
Craft, D. L., et al.; Improved Planning Time and Plan Quality Through Multicriteria Optimization for Intensity-Modulated Radiotherapy; 2012; Int. J. Radiat. Oncol. Biol. Phys.; 82(1)83-90.
Defrise, M., et al.; Time-of-flight PET data determine the attenuation sinogram up to a constant; 2012; Physics in Medicine & Biology; 57(4)885-902.
Gopal, R., et al.; Plan space: representation of treatment plans in multidimensional space; 2002; Int'l. Journal of Radiation Oncology Biology Physics; 53(5)1328-1336.
Hamilton, R., et al.; Intensity Modulated Radiation Therapy: A Clinical Perspective; 2005; vol. 1, Chapt. 10 "Treatment Planning"; pp. 151.
Moore, K. L., et al.; Quantitative Metrics for Assessing Plan Quality; 2012; Semin. Radiat. Oncology; 22:62-69.
Natterer, F.; Computerized Tomography with Unknown Sources; 1983; SIAM Journal on Applied Mathematics; 43(5)1201-1212.
Nuyts, J., et al.; Simultaneous Maximum a Posteriori Reconstruction of Attenuation and Activity Distributions from Emission Sinograms; 1999; IEEE Trans. on Medical Imaging; 18(5)393-403.
Oelfke, U., et al.; Inverse Planning for Photon and Proton Beams; 2001; Medical Dosimetry; 26(2)113-124.
Petit, S. F., et al.; Increased organ sparing using shape-based treatment plan optimization for intensity modulated radiation therapy of pancreatic adenocarcinoma; 2012; Radiotherapy and Oncology; 102:38-44.
Rosen, I., et al.; Interactively exploring optimized treatment plans; 2005; Int'l Journal of Radiation Oncology Biology Physics; 61(2)570-582.
Salomon, A., et al.; Simultaneous Reconstruction of Activity and Attenuation for PET/MR; 2011; IEEE Trans. on Medical Imaging; 30(3)804-813.
Welch, A., et al.; Attenuation Correction in PET Using Consistency Information; 1998; IEEE Trans. on Nuclear Science; 45(6)3134-3141.
Wu, B., et al.; Data-driven Approach to Generating Achievable Dose-Volume Histogram Objectives in Intensity-modulated Radiotherapy Planning; 2010; Int. J. Radiation Oncology Biol. Phys.; 79:1241-1247.
Wu, B., et al.; Knowledge-based and Patient-Geometry Specific IMRT Treatment; 2010; Med. Phys.; 37:3368.
Wu, B., et al.; Patient geometry-driven information retrieval for IMRT treatment plan quality control; 2009; Med. Phys.; 36(12)5497-5505.
Wu, B., et al.; Using overlap volume histogram and IMRT plan data to guide and automate VMAT planning; a head-and-neck case study; 2013; Medical Physics; 40(2)021714-1-7.
Zhang, H. H., et al.; Modeling Plan-Related Clinical Complications using Machine Learning Tools in a Multi-Plan IMRT Framework; 2009; Int. J. Radiat. Oncol. Biol. Phys.; 74(5)1617-1626.
Zhang, X., et al.; A sensitivity-guided algorithm for automated determination of IMRT objective function parameters; 2006; Med. Phys.; 33(8)2935-2944.

US 9,943,702 B2

AUTOMATIC OPTIMAL IMRT/VMAT TREATMENT PLAN GENERATION

CROSS REFERENCE TO RELATED APPLICATIONS

This application is a national filing of PCT application Serial No. PCT/IB2013/059440, filed Oct. 18, 2013, published as WO 2014/068435 A2 on May 8, 2014, which claims the benefit of U.S. provisional application Ser. No. 61/719,528 filed Oct. 29, 2012, which is incorporated herein by reference.

The present application relates generally to radiation therapy. It finds particular application in conjunction with radiation therapy planning and will be described with particular reference thereto. However, it is to be understood that it also finds application in other usage scenarios and is not necessarily limited to the aforementioned application.

In radiation therapy planning, creating a patient specific treatment plan can be a time consuming and tedious task. Many of the steps are redundant and vary little from patient to patient or plan to plan. Many of these steps can be automated using macro languages or scripts, but certain aspects are difficult without tools for writing logical expressions, loops, and other common programming functionality.

One area that is difficult to automate in current treatment planning is intensity-modulated radiation therapy (IMRT) or volumetric-modulated arc therapy (VMAT) optimization. Optimization is an iterative process where a user attempts to specify planning goals in the form of dose or biological objectives to create an ideal dose to target structures, typically a uniform dose, and minimize the dose to critical structures.

For a plan with many target and critical structures, the optimization problem has a large number of dimensions that is difficult for a user to navigate. Further, current user interfaces can contain long lists of goals for a user to control. However, only a small subset are necessary, and many can be hidden or grouped together into common goals. Even more, while it is relatively easy to create a plan that meets the goals, it is typically difficult to create an optimal plan. Plans can typically be further optimized, usually significantly, but an optimal plan is hard to define. Therefore it is hard to judge the degree of optimization in the current trial. Either additional structures can be considered or dose to existing critical structures can be further reduced. Hence, optimization can be tedious, inconsistent, non-optimal, and non-intuitive.

The present application provides a new and improved system and method which overcome the above-referenced problems and others.

In accordance with one aspect, a therapy planning system for generating an optimal treatment plan is provided. The system includes at least one processor programmed to automatically formulate a plurality of objectives based on a plurality of clinical goals including dose profiles and priorities. The dose profiles and the priorities correspond to a plurality of structures, the plurality of structures including a plurality of target and/or critical structures identified within a planning image. The processor is further programmed to optimize a plurality of treatment plan parameters based on the plurality of objectives to generate a treatment plan and reformulate the plurality of objectives including at least one of modifying parameters of the plurality of objectives and adding one or more additional objectives to the plurality of objectives. The optimization is repeated based on the reformulated plurality of objectives to generate a reformulated treatment plan.

In accordance with another aspect, a therapy planning method for generating an optimal treatment plan is provided. A plurality of objectives are automatically formulated based on a plurality of clinical goals including dose profiles and priorities. The dose profiles and the priorities correspond to a plurality of structures, the plurality of structures including a plurality of target and/or critical structures identified within a planning image. A plurality of treatment plan parameters are optimized based on the plurality of objectives to generate a treatment plan, and the plurality of objectives are reformulated. The reformulating includes at least one of modifying parameters of the plurality of objectives and adding one or more additional objectives to the plurality of objectives. The optimization is repeated based on the reformulated plurality of objectives to generate a reformulated treatment plan.

In accordance with another aspect, a therapy planning system for generating an optimal treatment plan is provided. The system includes a formulating module which automatically formulates a plurality of objectives based on a plurality of clinical goals including dose profiles and priorities, the dose profiles and the priorities corresponding to target and/or critical structures. The system further includes an optimization module which optimizes a plurality of treatment plan parameters based on the plurality of objectives to generate a treatment plan, and a reformulating module which reformulates the plurality of objectives including at least one of modifying parameters of the plurality of objectives and adding one or more additional objectives to the plurality of objectives. Even more, the system includes a reoptimizing module which reoptimizes the plurality of treatment plan parameters based on the reformulated plurality of objectives.

One advantage resides in a more intuitive user interface for radiation therapy planning.

Another advantage resides in a more optimized radiation therapy plan.

Another advantage resides in less tedius radiation therapy planning.

Another advantage resides in more consistent radiation therapy planning.

Another advantage resides in lower patient doses.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
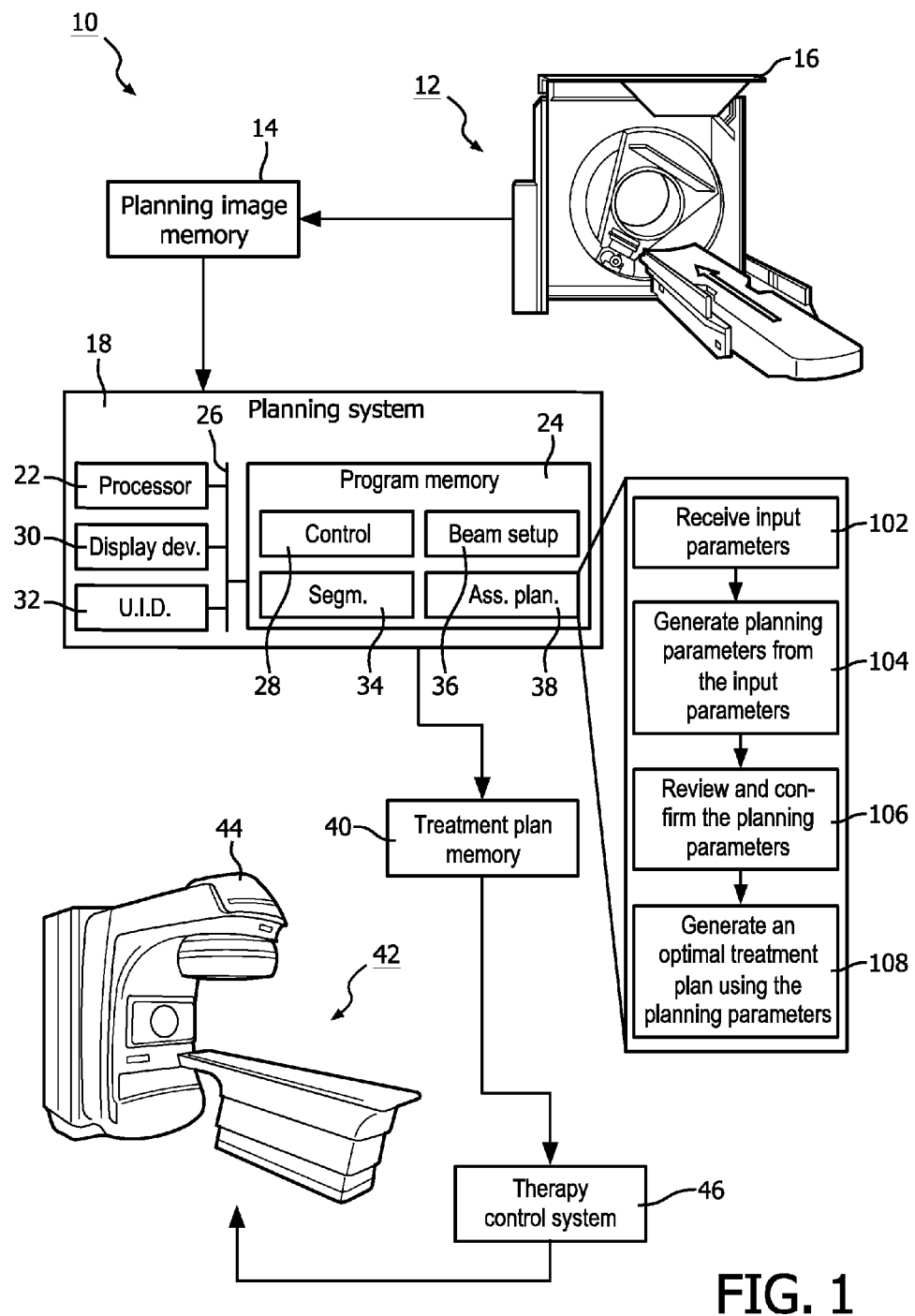
FIG. 1 illustrates a therapy system including an improved method for generating treatment plans.

With reference to FIG. 1, a therapy system 10, such as an intensity-modulated radiation therapy (IMRT) system or a volumetric-modulated arc therapy (VMAT) system, includes an imaging system 12 to generate one or more planning images of a region of interest of a patient. The planning images are volumetric (i.e., three-dimensional) and typically stored in a planning image memory 14 of the therapy system 10. The region of interest includes one or more target structures and, typically, one or more critical structures. Each of the target structures is a lesion or other tissue region, such as a tumor, to be irradiated. Each of the critical structures is an organ or other tissue region which is at risk of damage from the radiation intended for the target structures, such as radiation traveling to the target structures, which has passed through the target structures, or which passes closely adjacent the target structures.

The imaging system 12 generates the planning images using one or more imaging modalities, such as computed tomography (CT), positron emission tomography (PET), magnetic resonance (MR), single photon emission computed tomography (SPECT), cone-beam computed tomography (CBCT), and the like. Hence, the imaging system 12 includes one or more scanners 16 corresponding to the imaging modalities, as well as a backend system reconstructing raw image data from the scanners into the planning images. As illustrated, the imaging system 12 generates the planning images using at least CT and includes a CT scanner 16.

A planning system 18 of the therapy system 10 generates an optimal treatment plan for the patient on the planning images, which are typically received from the planning image memory 14. The optimal treatment plan suitably includes a plurality of treatment fractions, each identifying planning target volumes (PTVs) for the target structures, margins around the target structures, dose profiles for the target structures, dose limits for the critical structures, and therapy beam directions and intensities, and is typically stored in a treatment plan memory 20 of the therapy system 10. The planning system 18 includes at least one processor 22 and at least one program memory 24. The program memory 24 includes processor executable instructions that, when executed by the processor 22, generate the optimal treatment plan. The processor 22 executes the processor executable instructions to generate the optimal treatment plan. The planning system 18 further includes at least one system bus 26 interconnecting the processor 22, the program memory 24, and any other components of the planning system 18.

A control module 28 of the processor executable instructions controls overall operation of the planning system 18, including generation of the optimal treatment plan. The control module 28 suitably displays a graphical user interface (GUI) to a user of the planning system 18 using a display device 30 of the planning system 18. Further, the control module 28 suitably allows the user to interact with the GUI using a user input device 32 of the planning system 18. For example, the user can interact with the GUI to specify parameters controlling the generation of the optimal treatment plan.

A segmentation module 34 of the processor executable instructions segments the planning images to identify the boundaries of the structures (i.e., the target structures and, typically, the critical structures) and bone or other radiation attenuating structures within the planning images. The segmentation can be performed automatically and/or manually. As to automatic segmentation, a segmentation routine is employed to identify the boundaries of the structures. The segmentation routine can be one of any number of known segmentation routines, such as a model or atlas based segmentation routine. As to manual segmentation, a user uses the user input device 32 to identify the boundaries of the structures. In some embodiments, the segmentation module 34 employs the user interface to display the planning images to the user. The user can then identify the boundaries of the structures on the planning images using the user input device 32.

It is also contemplated that the segmentation can be performed using a combination of automatic and manual segmentation. Namely, the boundaries of the structures can be automatically identified as described above. The automatically identified boundaries can then be displayed to the user, optionally overlaid on the planning images, using the display device 30 and the user can modify the identified boundaries, as necessary, using the user input device 32.

A therapy beam setup module 36 of the processor executable instructions configures one or more therapy beams used for therapy delivery. This can be performed automatically and/or manually. As to automatic therapy beam setup, an appropriate routine is employed to automatically configure parameters configuring the therapy beam. As to manual segmentation, a user uses the user input device 32 to specify parameters configuring the therapy beams. It is also contemplated that therapy beam setup can be performed using a combination of automatic and manual therapy beam setup. Namely, automatic selection can be employed, as described above. The automatically configured parameters can then be displayed to the user using the display device 30 and the user can modify the parameters, as necessary, using the user input device 32.

An assisted planning module 38 of the processor executable instructions generates the optimal treatment plan. This includes receiving 102 input parameters for generation of the treatment parameter. The input parameters include the boundaries of the structures (i.e., the target structures and, typically, the critical structures) within the planning images, which are identified using the segmentation module 34, as well as therapy beam configuration parameters, which are determined using the therapy beam setup module 36.

The input parameters further include parameters received from the user input device 32. These parameters include labeling each of the structures identified in the planning images as one of a target structure and a critical structure. Further, these parameters include, for each structure, specification of: 1) a dose profile to be achieved based on the user's expertise or clinical guidelines; and 2) a priority relative to the other structures. The priority of a structure indicates the priority of its corresponding dose profile relative to the other structures. The priorities can then be employed to resolve a conflict between, for example, covering a target structure and sparing a critical structure.

Figure 2:
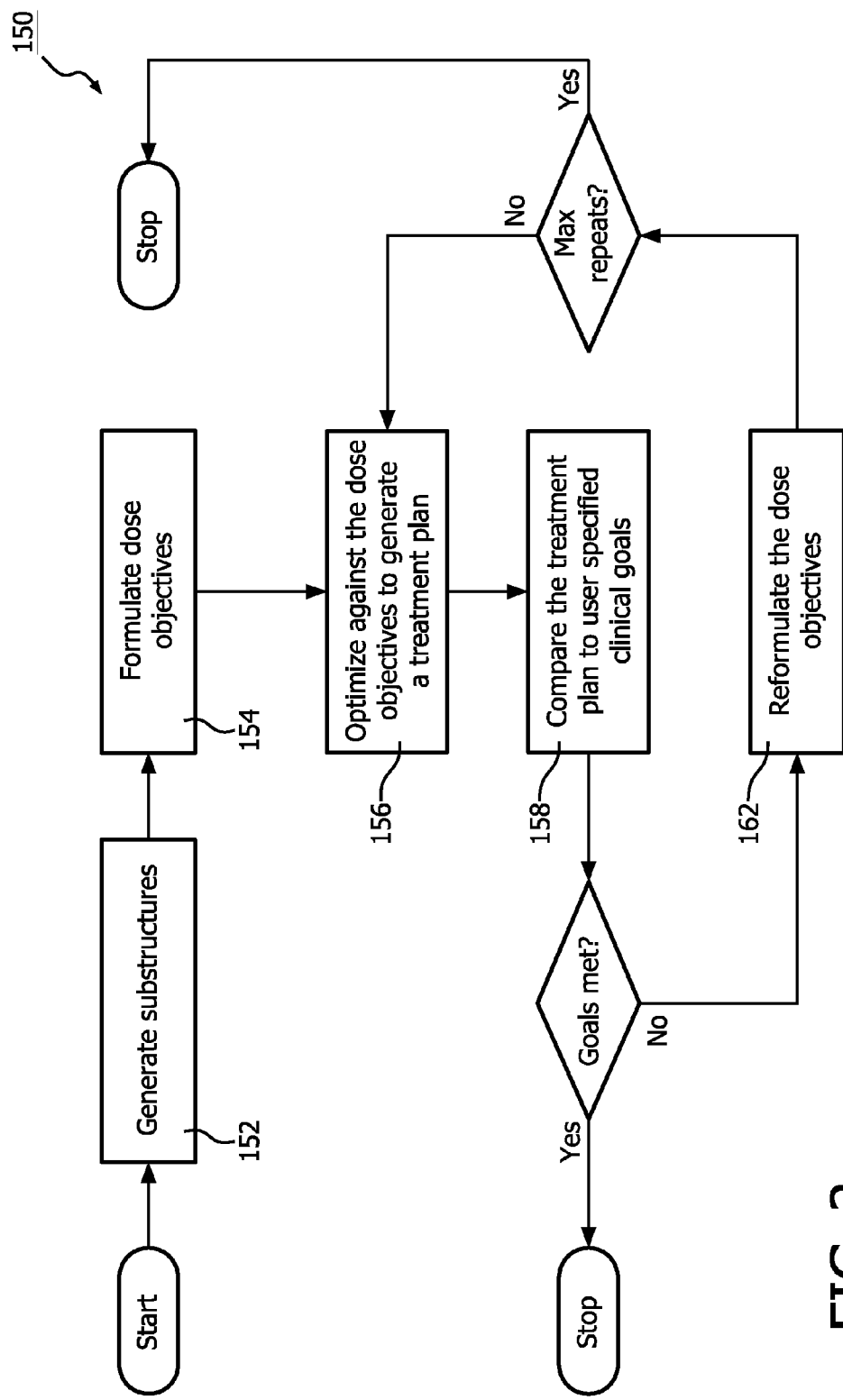
FIG. 2 illustrates a treatment plan generation routine.

Based on the input parameters, the assisted planning module 38 automatically generates 104 planning parameters to control a treatment plan generation routine 150, discussed hereafter and illustrated in FIG. 2. The planning parameters include, for example, iso-center, dose grid, and so on.

In some embodiments, the user reviews and confirms 106 the planning parameters using the user input device 32. Namely, the planning parameters are displayed to the user using the display device 30. The user can then modify the planning parameters using the user input device 32 as necessary. Additionally, or alternatively, overlap statistics describing overlap between the structures are displayed to the user using the display device 30. The overlap statistics can assist the user in making priority decisions, such as, for example, the decision to spare a structure or sacrifice it for target coverage.

Overlap between structures is determined based on the input parameters using any number of approaches. According to one approach, volumetric overlap between the structure and the other structure is determined, the volumetric overlap corresponding to the overlap region. According to another approach, a projection image of the structure and the other structure from the perspective of one of the therapy beams is created. The overlap between the structure and other structure is then determined within the projection image and the overlap region is back projected to the volumetric planning images. In some embodiments, this approach is employed for each therapy beam.

Based on the planning parameters (as confirmed, where applicable), the assisted planning module 38 generates 108 the optimal treatment plan according to the treatment plan generation routine 150 illustrated in FIG. 2. As will be seen, the treatment plan generation routine 150 progressively refines a set of dose objectives to drive an inverse planning optimization towards the optimal solution in a complex multi-dimensional search space. The optimal treatment plan is typically stored in a treatment plan memory 40 of the therapy system 10.

With further reference to FIG. 2, the treatment plan generation routine 150 includes generating 152 an optimal set of substructures from the structures identified in the planning images. The substructures are based on the geometrical relationship and relative priorities of the structures, and advantageously help the optimization run with as few conflicts as possible and achieve a faster convergence.

To generate the substructures, each structure is analyzed for overlap with other structures using any number of approaches, such as one or more of the approaches discussed above. For each overlap between the structure and another structure, the overlap region is removed from the structure to create a substructure if the priority of the structure is less than the priority of the other structure. For example, if a critical structure overlaps with a target structure having a higher priority, a substructure is generated, the substructure being the critical structure less the overlapping region. A padding margin is suitably removed from each of the substructure to account for the high dose gradient at the overlapping boundaries of the structures.

After generating the optimal set of substructures, dose objectives are formulated 154 using the structures and the substructures. Each dose objective includes a plurality of parameters, including a dose, a weight, biological factors, such as "a" value, and the like. Typically, the translation from user input goals to dose objectives for the optimizer is performed intelligently based on the dose profiles of the structures and substructures. However, the translation to dose objectives for the optimizer can also be performed intelligently based on distance profiles between the target and critical structures and substructures. The weights of the dose objectives are assigned based on the priority of the corresponding structures and substructures.

The dose profiles and priorities of the structures are incorporated into, or otherwise defined by, the planning parameters, and the substructures assume the dose profiles and priorities of the corresponding structures. Further, the distance profiles between target and critical structures and substructures are defined by the planning parameters.

Using the dose objectives, inverse planning optimization is performed 156 to generate a treatment plan. The inverse planning optimization routine can be any number of well-known routines. The goal is to reduce the dose to the critical structures and other non-target structures to a point just before significant coverage of the target structures is compromised, while maintaining intended dose coverage of the target structures.

The inverse planning optimization routine includes determining a tuning force for each of the dose objectives. The tuning force is based on one or more of the dose, the weight, the current value (i.e., an objective assessment against the optimizer's solution), and any number of biological parameters, such as "a" value. If the tuning force corresponds to a critical structure, the tuning force pushes the dose of the corresponding region towards a lower level. However, if the tuning force corresponds to a target structure, the tuning force pushes the dose of the corresponding region towards the dose profile of the target structure.

After the treatment plan is generated, the treatment plan is compared 158 to the user specified clinical goals, such as the dose profiles of the structures or heterogeneity indexes, to quantitatively assess how well the treatment plan achieves the clinical goals. The comparison and quantitative assessment can, for example, be performed by a scoring routine designed to score how well the treatment plan achieves the clinical goals. The clinical goals are incorporated into, or otherwise defined by, the planning parameters. A determination 160 is then made as to whether the clinical goals are met based on the comparison 158. For example, insofar as the similarity between the treatment plan and the clinical goals exceeds a predetermined level, the treatment plan represents the optimal treatment plan. Otherwise, the dose objectives are reformulated 162.

Reformulating the dose objectives guides towards an optimal solution (as per the user priority) by driving the tuning forces while maintaining a state of equilibrium. If a critical structure does not overlap with a target structure, the tuning force of the corresponding dose objective is adjusted towards a lower dose. Otherwise, the tuning force is adjusted based on the priority of the critical structure and clinical guideline requirements to achieve the optimal trade-off.

To reformulate the dose objectives, the current value of each of the objective functions is determined. As noted above, the current value is an objective assessment against the optimizer's solution (i.e., the treatment plan). The current value is compared to a predetermined convergence value, for example, specified by the user using the user input device. If the current value is less than the predetermined convergence value, the parameters of the dose objective are modified to increase the current value of the dose objective to approximately the predetermined convergence value. If the current value is greater than the predetermined convergence value, the parameters of the dose objective are modified to decrease the current value of the dose objective to approximately the predetermined convergence value.

In addition to modifying the parameters of the dose objectives, additional dose objectives can be added for high priority structures and/or the weights of existing objectives can be adjusted. For example, a high weight objective can be added for a high priority structure if the corresponding clinical goal is not met. As another example, hot and/or cold spots can be identified and objectives corresponding to these spots can be added to achieve a conformal dose distribution to target structures. As another example, dose spillage outside of target structures can be identified and objectives can be added to reduce the identified spillage.

In some embodiments, a user can employ the user input device 32 to modify the parameters of the dose objectives and/or generate new dose objectives. For example, the user can be presented with the objectives with the display device 30. The user can then modify the objectives manually using the user input device 32. As another example, the user can be presented with an abstracted user interface with the display device 30 which presents conflicting structure pairs. For each structure pair, the user can then specify priorities between the structures, which can be used to update the parameters of the dose objectives, using the user input device 32.

After reformulating the dose objectives, the foregoing actions, beginning with the performing 156 inverse planning optimization, are repeated for the reformulated dose objectives. In some embodiments, this repeating is performed for up to a predetermined number of times, such that a determination 162 is made as to whether the repeating has been performed more than the predetermined number of times before repeating. Insofar as it has, the optimal treatment plan is the most recent treatment plan. Otherwise, the repeating continues. Alternatively, the repeating is performed until the plan change from one repetition to the next falls below a minimum improvement criteria.

Referring to FIG. 1, a delivery system 42 executes the optimal treatment plan to deliver therapy, such as ablation therapy, external beam radiation therapy and/or brachytherapy, to the patient. The therapy typically includes radiation, such as one or more of x-rays, protons, high-intensity focused ultrasound (HIFU), and the like. The delivery system 42 includes a delivery apparatus 44, such as a linear particle accelerator, and a control system 44, which controls the delivery apparatus 46 in accordance with the optimal treatment plan. The optimal treatment plan is typically received from the treatment plan memory 40, but other sources are contemplated.

As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor includes one or more of a microprocessor, a microcontroller, a graphic processing unit (GPU), an application-specific integrated circuit (ASIC), an FPGA, and the like; a controller includes: (1) a processor and a memory, the processor executing computer executable instructions on the memory embodying the functionality of the controller; or (2) analog and/or digital hardware; a user input device includes one or more of a mouse, a keyboard, a touch screen display, one or more buttons, one or more switches, one or more toggles, voice recognition engines, and the like; a database includes one or more memories; and a display device includes one or more of a LCD display, an LED display, a plasma display, a projection display, a touch screen display, and the like.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A therapy planning system for generating an optimal treatment plan, said system comprising:
at least one processor programmed to:
automatically formulate a plurality of dose objectives based on a plurality of clinical goals including dose profiles and priorities of a plurality of structures, the plurality of structures including a plurality of target structures and/or critical structures identified within a planning image, a priority indicating the priority of the dose profile of its corresponding structure relative to other structures;
optimize a plurality of treatment plan parameters based on the plurality of dose objectives to generate a treatment plan;
compare the treatment plan to the clinical goals to determine a score assessing the extent to which the treatment plan achieves the clinical goals;
reformulate the plurality of dose objectives including at least one of modifying parameters of the plurality of dose objectives and adding one or more additional dose objectives to the plurality of objectives in response to the score falling within a predetermined range; and,
repeat the optimizing based on the reformulated plurality of dose objectives to generate a reformulated treatment plan.

2. The therapy planning system according to claim 1, wherein the reformulating and the optimizing are repeated for a predetermined number of iterations.

3. The therapy planning system according to claim 1, wherein the processor is further programmed to:
generate additional structures of the plurality of structures from the target and/or critical structures, the generating including:
determining an overlapping pair of target structures and/or critical structures; and,
removing the overlapping region from the structure of the overlapping pair with a lower user specified priority to create an additional structure used in the automatically formulating a plurality of dose objectives.

4. The therapy planning system according to claim 1, wherein the optimizing includes:
determining a tuning force for each dose objective, the tuning force based on one or more of a dose, a weight of a dose objective and a current value of a dose objective, the current value assessing the extent to which a current treatment plan achieves the dose objective; and,
adjusting dose to regions corresponding to the plurality of structures, wherein tuning forces corresponding to critical structures push towards lower doses while tuning forces corresponding to target structures simultaneously push towards higher doses.

5. The therapy planning system according to claim 1, wherein the reformulating includes:
determining a current value for each of the plurality of dose objectives, the current value assessing the extent to which the treatment plan achieves the dose objective; and,
modifying the parameters of the plurality of dose objectives to approximately match the current values to corresponding predetermined convergence values.

6. The therapy planning system according to claim 1, wherein the parameters of the plurality of dose objectives includes dose parameters and corresponding weight parameters.

7. The therapy planning system according to claim 1, wherein:
the at least one processor is programmed to reformulate the plurality of objectives by adding one or more additional dose objectives in response to the score falling within the predetermined range; and
the additional dose objectives includes at least one of:
a dose objective for a high priority structure with a corresponding clinical goal that is not met by the treatment plan;
a dose objective for a hot or cold region; and,
a dose objective for a region of dose spillage from dose to a target structure.

8. The therapy planning system according to claim 1, wherein the reformulating includes:
receiving relative priorities for a pair of conflicting structures from a user;
modifying the parameters based on the received priorities.

9. The therapy planning system according to claim 1, further comprising:
a therapy delivery apparatus controlled configured to deliver radiation according to the reformulated treatment plan.

10. A therapy planning method, performed by at least one processor, for generating an optimal treatment plan, said method comprising:
automatically formulating a plurality of dose objectives based on a plurality of clinical goals including dose profiles and priorities of a plurality of target structures, the plurality of structures including a plurality of target and/or critical structures identified within a planning image, a priority indicating the priority of the dose profile of its corresponding structure relative to other structures;
optimizing a plurality of treatment plan parameters based on the plurality of dose objectives to generate a treatment plan;
comparing the treatment plan to the clinical goals to determine a score assessing the extent to which the treatment plan achieves the clinical goals;
reformulating the plurality of dose objectives including at least one of modifying parameters of the plurality of dose objectives and adding one or more additional dose objectives to the plurality of dose objectives in response to the score falling within a predetermined range; and,
repeating the optimizing based on the reformulated plurality of dose objectives to generate a reformulated treatment plan.

11. The therapy planning method according to claim 10, wherein the reformulating and the optimizing are repeated for a predetermined number of iterations or until the clinical goals are met.

12. The therapy planning method according to claim 10, further including:
generating additional structures of the plurality of structures from the target and/or critical structures, the generating including:
determining an overlapping pair of target structures and/or critical structures; and,
removing the overlapping region from the structure of the overlapping pair with a lower user specified priority to create an additional structure used in the automatically formulating a plurality of dose objectives; and
controlling a radiation therapy device to deliver radiation to a patient based on the reformulated treatment plan.

13. The therapy planning method according to claim 10, wherein the optimizing includes:
determining a tuning force for each dose objective, the tuning force based on one or more of a dose, a weight of a dose objective and a current value of a dose objective, the current value assessing the extent to which a current treatment plan achieves the dose objective;
adjusting dose to regions corresponding to the plurality of structures, wherein tuning forces corresponding to critical structures push towards lower doses while tuning forces corresponding to target structures simultaneously push towards higher doses; and,
controlling a radiation therapy device to deliver radiation to a patient based on the reformulated treatment plan.

14. The therapy planning method according to claim 10, wherein the reformulating includes:
determining a current value for each of the plurality of dose objectives, the current value assessing the extent to which the treatment plan achieves the dose objective; and,
modifying the parameters of the plurality of dose objectives to approximately match the current values to corresponding predetermined convergence values.

15. The therapy planning method according to claim 10, wherein the parameters of the plurality of dose objectives includes dose parameters and corresponding weight parameters.

16. A non-transitory computer readable medium carrying software which controls the at least one processor to perform the method according to claim 10.

17. A therapy planning system for generating an optimal treatment plan, said system comprising:
a formulating module which automatically formulates a plurality of close objectives based on a plurality of clinical goals including dose profiles and priorities of a plurality of target structures and/or critical structures, a priority indicating the priority of the dose profile of its corresponding structure relative to other structures;
an optimization module which optimizes a plurality of treatment plan parameters based on the plurality of dose objectives to generate a treatment plan;
a comparing module which compares the treatment plan to the clinical goals to determine a score assessing the extent to which the treatment plan achieves the clinical goals;
a reformulating module which reformulates the plurality of dose objectives including at least one of modifying parameters of the plurality of dose objectives and adding one or more additional dose objectives to the plurality of dose objectives in response to the score falling within a predetermined range; and,
a reoptimizing module which reoptimizes the plurality of treatment plan parameters based on the reformulated plurality of dose objectives.

18. The therapy planning system according to claim 1, wherein:
the at least one processor is programmed to reformulate the plurality of dose objectives by adding one or more additional dose objectives in response to the score falling within the predetermined range; and
the additional dose objectives includes all of:
a dose objective for a high priority structure with a corresponding clinical goal that is not met by the treatment plan;
a dose objective for a hot or cold region; and,
a dose objective for a region of dose spillage from dose to a target structure.

19. The therapy planning system according to claim 1, wherein the reformulating and the optimizing are repeated until the clinical goals are met.

20. The therapy planning system according to claim 1, wherein the reformulating the plurality of objectives includes adjusting a dose objective of the plurality of dose objectives towards a lower dose.

* * * * *